(12) United States Patent
Tabata et al.

(10) Patent No.: US 8,895,508 B2
(45) Date of Patent: Nov. 25, 2014

(54) METHODS FOR CORNEAL ENDOTHELIAL PROLIFERATION USING BFGF SUSTAINED-RELEASE GELATIN HYDROGEL PARTICLES

(75) Inventors: Yasuhiko Tabata, Kyoto (JP); Shigeru Kinoshita, Osaka (JP); Noriko Koizumi, Kyoto (JP); Yuji Sakamoto, Hyogo (JP); Naoki Okumura, Kyoto (JP); Hiroaki Takahashi, Hyogo (JP)

(73) Assignees: Yasuhiki Tabata, Uji (JP); Senju Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 13/386,844

(22) PCT Filed: Jul. 24, 2009

(86) PCT No.: PCT/JP2009/063624
§ 371 (c)(1),
(2), (4) Date: Apr. 13, 2012

(87) PCT Pub. No.: WO2011/010399
PCT Pub. Date: Jan. 27, 2011

(65) Prior Publication Data
US 2012/0190621 A1    Jul. 26, 2012

(51) Int. Cl.
*A61K 38/18*  (2006.01)
*A61K 9/00*   (2006.01)
*A61K 9/06*   (2006.01)
*A61K 47/42*  (2006.01)

(52) U.S. Cl.
CPC ........... *A61K 38/1825* (2013.01); *A61K 9/0048* (2013.01); *A61K 9/06* (2013.01); *A61K 47/42* (2013.01)
USPC ........................................................ 514/9.1

(58) Field of Classification Search
None
See application file for complete search history.

(56) References Cited

U.S. PATENT DOCUMENTS

| 4,853,224 A | 8/1989 | Wong |
| 6,831,058 B1 | 12/2004 | Ikada et al. |
| 2004/0253294 A1 | 12/2004 | Tabata |
| 2008/0107703 A1 | 5/2008 | Tabata |

FOREIGN PATENT DOCUMENTS

| JP | 02-000702 A | 1/1990 |
| JP | 2005-104910 A | 4/2005 |
| WO | WO 94/27630 A1 | 12/1994 |
| WO | WO 03/007982 A1 | 1/2003 |
| WO | WO 2006/085653 A1 | 8/2006 |

OTHER PUBLICATIONS

Hosaka et al., *Circulation*, 110: 3322-3328 (Nov. 1, 2004).
Rieck et al., *Current Eye Research*, 11(12): 1161-1172 (1992).
Tabata et al., *Advanced Drug Delivery Reviews*, 31: 287-301 (1998).
Takahashi et al., *Invest. Ophthamol. Vis. Sci.*, 50: E-Abstract 1827-A495 (2009).
Yang et al., *Ophthalmic Research*, 32(1): 19-24 (2000).
Japanese Patent Office, International Search Report in International Patent Application No. PCT/JP2009/063624 (Sep. 29, 2009).

*Primary Examiner* — Christine J Saoud
(74) *Attorney, Agent, or Firm* — Leydig, Voit & Mayer, Ltd.

(57) ABSTRACT

The present invention aims to provide a corneal endothelium cell proliferation accelerator and a therapeutic agent for a disease relating to corneal endothelium damage, which are administered into the anterior chamber. bFGF is released in a sustained manner by forming bFGF sustained-release gelatin hydrogel particles wherein bFGF is carried on gelatin hydrogel. Therefore, the proliferation of corneal endothelium cells can be accelerated persistently by administration of a preparation containing the bFGF sustained-release gelatin hydrogel particles into the anterior chamber, and diseases relating to corneal endothelium damage can be treated.

6 Claims, 6 Drawing Sheets
(3 of 6 Drawing Sheet(s) Filed in Color)

METHODS FOR CORNEAL ENDOTHELIAL PROLIFERATION USING BFGF SUSTAINED-RELEASE GELATIN HYDROGEL PARTICLES

TECHNICAL FIELD

The present invention relates to a use of basic fibroblast proliferation factor (bFGF) sustained-release gelatin hydrogel for the acceleration of corneal endothelial cell proliferation and the treatment of diseases associated with corneal endothelial damage.

BACKGROUND ART

The cornea consists of the three layers of epithelium, stroma and endothelium; the corneal endothelium is a single cell layer located on the innermost side of the cornea, working to retain the water content of the cornea and maintain the transparency. Corneal endothelial cells are poor in proliferative capability in vivo; when some corneal endothelial cells are damaged, neighboring cells elongate to fill in the damaged area. For this reason, corneal endothelial cells, once damaged, become less dense and no longer capable of maintaining the transparency. This pathologic condition is called bullous keratopathy, causing serious visual impairment.

As a factor known to allow corneal endothelial cells with low proliferative capability to proliferate, bFGF is used to culture corneal endothelial cells in vitro. Available in the past literature is a report on an attempt to accelerate corneal endothelial cell proliferation by administration of bFGF solution into the anterior chamber in vivo (non-patent document 1). However, the aqueous humor is constantly produced and excreted, 20% of the aqueous humor being exchanged in 1 hour. To allow bFGF to act on corneal endothelial cells for a long time, an appropriate carrier that allows the drug to be released in a sustained manner is needed. Meanwhile, since bFGF is known to act as a potent neovascularization factor in a variety of organs, there is a demand for establishing a method of appropriately administering bFGF and amounts administered such that such various side effects are suppressed to the minimum levels and the therapeutic effect is maximized in corneal endothelium regenerative medicine.

The present inventors found that gelatin hydrogel (crosslinked gelatin gel) is useful as a good carrier capable of releasing protein in a sustained manner, and have already developed a bFGF sustained-release gelatin hydrogel (bFGF-containing crosslinked gelatin gel) preparation incorporating this carrier. Although this bFGF sustained-release gelatin hydrogel preparation is highly useful in accelerating neovascularization and treating bone fractures, no report has been presented to date on the application thereof to the acceleration of corneal endothelial cell proliferation (patent documents 1-4, non-patent documents 2 and 3).

PRIOR DOCUMENTS

Patent Documents

[patent document 1]: JP-A-2005-104910
[patent document 2]: WO03/007982
[patent document 3]: WO94/27630
[patent document 4]: WO2006/085653

Non-Patent Documents

[non-patent document 1]: Curr Eye Res. Vol. 11, pp. 1161-72, 1992
[non-patent document 2]: Advanced Drug Delivery Reviews, vol. 31, pp. 287-301, 1998
[non-patent document 3]: Circulation, vol. 110, pp. 3322-3328, 2004

SUMMARY OF THE INVENTION

Problems to Be Solved by the Invention

It is an object of the present invention to provide a bFGF preparation that accelerates the proliferation of corneal endothelial cells and is useful in treating a disease associated with corneal endothelial damage.

Means of Solving the Problems

The present inventors extensively investigated to solve the above-described problems, found that it is possible to persistently accelerate the proliferation of corneal endothelial cells by administering a bFGF sustained-release gelatin hydrogel particle comprising a bFGF-carrying gelatin hydrogel into the anterior chamber, and have developed the present invention.

Accordingly, the present invention provides the following:
[1] A corneal endothelial cell proliferation accelerator comprising a bFGF sustained-release gelatin hydrogel particle containing a bFGF-carrying gelatin hydrogel, to be administered into the anterior chamber.
[2] The accelerator described in [1], wherein the amount of bFGF administered is 30 to 300 ng per eye.
[3] A therapeutic agent for a disease associated with corneal endothelial damage, comprising a bFGF sustained-release gelatin hydrogel particle containing a bFGF-carrying gelatin hydrogel, to be administered into the anterior chamber.
[4] The agent described in [3], wherein the amount of bFGF administered is 30 to 300 ng per eye.
[5] The agent described in [3], wherein the disease associated with corneal endothelial damage is bullous keratopathy.
[6] A method of accelerating the proliferation of corneal endothelial cells, comprising administering an effective amount of a bFGF sustained-release gelatin hydrogel particle containing a bFGF-carrying gelatin hydrogel into the anterior chamber of a subject.
[7] The method described in [6], wherein the amount of bFGF administered is 30 to 300 ng per eye.
[8] A method of treating a disease associated with corneal endothelial damage, comprising administering an effective amount of a bFGF sustained-release gelatin hydrogel particle containing a bFGF-carrying gelatin hydrogel into the anterior chamber of a subject.
[9] The method described in [8], wherein the amount of bFGF administered is 30 to 300 ng per eye.
[10] The method described in [8], wherein the disease associated with corneal endothelial damage is bullous keratopathy.
[11] A use of a bFGF sustained-release gelatin hydrogel particle containing a bFGF-carrying gelatin hydrogel for producing a corneal endothelial cell proliferation accelerator to be administered into the anterior chamber of a subject.
[12] The use described in [11], wherein the amount of bFGF administered is 30 to 300 ng per eye.
[13] A use of a bFGF sustained-release gelatin hydrogel particle containing a bFGF-carrying gelatin hydrogel for producing a therapeutic agent for a disease associated with corneal endothelial damage, to be administered into the anterior chamber of a subject.

[14] The use described in [13], wherein the amount of bFGF administered is 30 to 300 ng per eye.
[15] The use described in [13], wherein the disease associated with corneal endothelial damage is bullous keratopathy.

Effect of the Invention

According to the present invention, it is possible to persistently accelerate the proliferation of corneal endothelial cells and treat a disease associated with corneal endothelial damage.

BRIEF DESCRIPTION OF THE DRAWINGS

The patent or application file contains at least one drawing executed in color. Copies of this patent or patent application publication with color drawing(s) will be provided by the Office Upon request and payment of the necessary fee.

MODES FOR EMBODYING THE INVENTION

Figure 1:
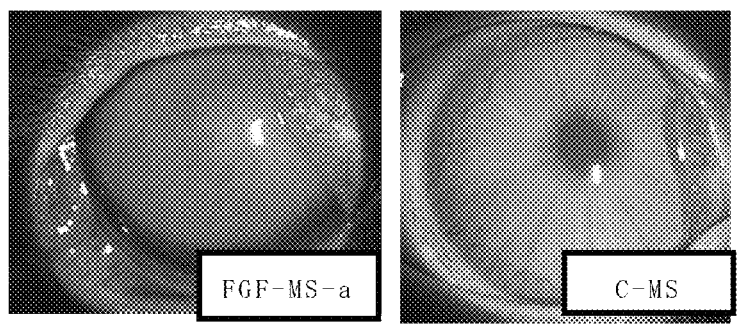
FIG. 1 is a photograph of the anterior ocular segment of normal rabbits on day 6 from the administration of C-MS or FGF-MS-a.

The present invention relates to an agent comprising a bFGF sustained-release gelatin hydrogel particle (bFGF sustained-release gelatin microsphere) containing a bFGF-carrying gelatin hydrogel, to be administered into the anterior chamber. The agent of the present invention is useful as a corneal endothelial cell proliferation accelerator and as a therapeutic agent for a disease associated with corneal endothelial damage.

bFGF is a publicly known cytokine, and the amino acid sequence and the like thereof are also publicly known. The bFGF used in the present invention is exemplified by bFGF extracted from bFGF-expressing organs such as the pituitary, brain, retina, corpus lutea, adrenal, kidney, placenta, prostate, and thymus, bFGF produced using gene engineering techniques such as recombinant DNA technology, and modified forms thereof capable of accelerating the proliferation of corneal endothelial cells. Modified forms of bFGF include, for example, those resulting from addition of an amino acid, substitution of an amino acid by another amino acid, or deletion of an amino acid, and the like in the amino acid sequence of the aforementioned bFGF obtained by extraction or a gene engineering technique. In the present invention, these bFGFs or modified forms thereof may be used alone, and may be used as a mixture thereof.

The bFGF used in the present invention is normally of mammalian origin. Mammals include, for example, laboratory animals such as mice, rats, hamsters, guinea pigs, and other rodents, and rabbits; domestic animals such as swine, bovines, goat, horses, sheep, and minks; companion animals such as dogs and cats; and primates such as humans, monkeys, cynomolgus monkeys, rhesus monkeys, marmosets, orangutans, and chimpanzees.

The bFGF is preferably exemplified by those described in WO87/01728 (JP-A-63-500843), WO89/04832 (JP-A-2-504468), WO86/07595 (JP-A-63-500036), WO87/03885 (JP-A-63-501953), EP-A-237966 (JP-A-63-226287), EP-A-281822 (JP-A-2-193), EP-A-326907 (JP-A-2-909894), EP-A-394951 (JP-A-3-61494), EP-A-493737 (JP-A-5-124975) and the like.

Of these bFGFs, a polypeptide having an amino acid sequence shown in WO 94/27630, produced by a gene engineering technique described in WO87/01728, is preferred because of the stability and the ease of constant supply of a required amount of material. The bFGF having the amino acid sequence shown in WO94/27630 can be obtained by preparing a cDNA clone of human bFGF from a λgt10 cDNA library prepared from human renal mRNA, using a 1.4 kb basic subfragment of the bovine sequence, constructing an expression vector, and expressing the clone, as described specifically in Examples in WO87/01728.

The gelatin used in the present invention is not particularly limited as to the choice thereof, as far as sustained release of bFGF is possible; however, because bFGF is a basic protein, an acidic gelatin capable of stably forming a complex therewith is preferred. The isoelectric point of an acidic gelatin is normally about 5 (4.9 to 5.0). When using an acidic gelatin, the gelatin constituting gelatin hydrogel and bFGF form a complex in the gel, so that the rapid release of the bFGF is suppressed when transferred into the anterior chamber.

An acidic gelatin can be obtained by alkali treatment of a part such as the skin, tendon and bone, or a collagen of a variety of animal species, including bovines and swine. The gelatin used in the present invention is preferably an acidic gelatin prepared by alkali-treating bovine or swine collagen (preferably type I collagen). An acidic gelatin can also be obtained as the sample IEP5.0 from Nitta Gelatin Inc. and the like.

The gelatin hydrogel used in the present invention can be obtained by crosslinking the gelatin with a variety of chemical crosslinking agents (see, for example, WO94/27630). The chemical crosslinking agent is preferably, for example, glutaraldehyde, a water-soluble carbodiimide such as 1-ethyl-3-(3-dimethylaminopropyl)carbodiimide hydrochloride and 1-cyclohexyl-3-(2-morpholinoethyl)carbodiimide-meth-p-toluenesulfonate, a bisepoxy compound, formalin or the like, with greater preference given to glutaraldehyde and 1-ethyl-3-(3-dimethylaminopropyl)carbodiimide hydrochloride. In the present invention, glutaraldehyde can be particularly suitably used.

In the present invention, chemical crosslinking of gelatin hydrogel can be performed by reacting the gelatin hydrogel, previously molded into desired shape and size, with the above-described crosslinking agent in a solution. The molding can be performed by casting into a container an aqueous gelatin solution and the like. When using glutaraldehyde as the crosslinking agent, crosslinking can be performed by adding to an aqueous gelatin solution (for example, 25 mg gelatin/25 mL distilled water) a different volume of a 25% by weight aqueous glutaraldehyde solution, and stirring and allowing to stand the mixed solution. The volume of the aqueous glutaraldehyde solution added is normally 1 to 1000 μL, preferably 2.5 to 40 μL, more preferably 3 to 20 μL, relative to 25 mg gelatin/25 mL distilled water. If the volume of glutaraldehyde added is larger than 1000 μL, the crosslinking density of the hydrogel can be so high that the degradation rate is too slow when administered into aqueous humor, and this is undesirable. If the volume of glutaraldehyde added is smaller than 1 μL, a sufficient crosslinking density cannot be obtained, so that the degradation rate can be too fast when administered into aqueous humor and desired sustained release action sometimes cannot be obtained, and this is undesirable. Crosslinking of gelatin hydrogel may also be performed by mixing a pre-molding aqueous gelatin solution with an aqueous crosslinking agent solution.

An appropriate additive such as a solubilizer may be added to the glutaraldehyde solution. The solubilizer may be exemplified by, for example, ester-ether type surfactants such as polyoxyethylene sorbitan monooleate. The amount of solubilizer added is preferably 0.01 to 1% by weight (for example, 0.1% by weight). Crosslinking reaction time normally ranges from 0.5 to 96 hours, preferably from 3 to 48 hours (for example, 24 hours), when the crosslinking reaction is carried out under cooling (about 4° C.). When the crosslinking reaction is carried out at room temperature (about 24° C.), the crosslinking reaction time is normally 0.2 to 48 hours, preferably 2 to 30 hours.

It is preferable that after completion of the crosslinking reaction, the crosslinking reaction be stopped by the addition of an appropriate reaction stopper. The reaction stopper can be chosen as appropriate according to the choice of crosslinking agent; when using glutaraldehyde as the crosslinking agent, amino acids such as glycine, alanine, and arginine can be used. Thereof, glycine is suitably usable. Specifically, a glutaraldehyde solution and gelatin hydrogel are separated by a method such as centrifugation, and the recovered gelatin hydrogel may be resuspended in an aqueous glycine solution, and the suspension may be stirred. The concentration of the aqueous glycine solution used to stop the crosslinking reaction is normally 25 to 200 mM (for example, 100 mM); a preferred temperature of the aqueous glycine solution during resuspension of the gelatin hydrogel in the aqueous glycine solution and stirring of the suspension is 4 to 40° C., with preference given to stirring for about 0.5 to 12 hours. The gelatin hydrogel thus obtained can be suitably used as a carrier for releasing bFGF in a sustained manner when administered into aqueous humor, since the aldehyde residue of glutaraldehyde is blocked.

Gelatin can also be crosslinked by heat treatment or by irradiation of an energy ray such as ultraviolet ray, electron ray, and γ ray.

The gelatin hydrogel particles used in the present invention can be produced by, for example, a method described in WO94/27630, that is, a method wherein an oil such as olive oil is added to an aqueous gelatin solution, which is then stirred at 200 to 600 rpm to yield a W/O emulsion, and an aqueous chemical crosslinking agent solution (hereinafter also referred to as a crosslinking solution) is added thereto, or a method wherein an aqueous gelatin solution is previously added dropwise to an oil being stirred at 200 to 600 rpm to yield a W/O emulsion, after which gelatin particles are recovered via centrifugation and the like and dried, and the dry gelatin particles are suspended in an aqueous chemical crosslinking agent solution to yield gelatin hydrogel particles. The gelatin hydrogel particles obtained are used after drying under reduced pressure, preferably freeze-drying. Depending on the manufacturing process and raw material differences, the product can sometimes vary in physical properties such as molecular weight and water content, and either one is acceptable.

The particle diameter of the gelatin hydrogel particles is preferably about 2 to about 50 μm (preferably about 12 to about 20 μm) upon swelling because of the capability of administration into the anterior chamber, and from the viewpoint of avoiding the risks of interfering with the sight of the recipient of administration, of leading to increased intraocular pressure, and the like. If the diameter of the particles is smaller than about 2 μm, the particles, along with aqueous humor, can sometimes flow out from the anterior chamber, so that this is undesirable. Particles larger than about 50 μm are undesirable because they can sometimes lead to increased intraocular pressure. Because the degree of swelling depends on the water content and degree of crosslinking of the gelatin hydrogel particles, particles that become about 2 to about 50 μm upon swelling can be obtained by selecting as appropriate particles having a desired particle diameter from among the gelatin hydrogel particles obtained via the above-described process, according to water content and degree of crosslinking, and separately collecting the same by techniques such as sieving, or by performing the above-described process under conditions that allow a degree of crosslinking (water content) corresponding to the desired degree of swelling to be obtained, and separately collecting the particles by techniques such as sieving.

Herein, a particle diameter refers to a value obtained by measuring the particle diameters of at least 400 particles on a photomicrograph of water-swollen particles by an ordinary method, and calculating the mean.

Although it is desirable that the shape of the gelatin hydrogel particles be truly spherical to roughly spherical, the particles may be prolate spheroidal, cylindrical, or irregular.

Upon administration into the anterior chamber, the gelatin hydrogel particles are thought to adhere to the ocular tissue surrounding anterior aqueous humor and undergo gradual degradation by hydrolases and the like. Thereby, the bFGF being carried by the gelatin hydrogel is released in a sustained manner with the degradation of the gelatin hydrogel. The degradation rate is regulated mainly by the water content of the gel. A water content refers to a ratio of water weight in the gelatin hydrogel, relative to the total weight of the gel in a wet state; as this increases, the degree of crosslinking of the gelatin hydrogel decreases, and the gelatin hydrogel particles are more likely to be degraded and absorbed. Although gel having water content in the range of about 80 to about 99.9 w/w % can normally be used, the water content is more preferably about 90 to about 99.8 w/w %, particularly preferably about 95 to about 98 w/w %. If the water content of the particles is smaller than about 80 w/w %, a long time is taken to degrade the gelatin hydrogel particles, which in turn can slow the sustained release rate of bFGF and makes it impossible to maintain a sufficient bFGF concentration. If the water content of the particles is larger than about 99.9 w/w %, there can be some cases where the shape of the particles cannot be maintained, or bFGF is not gradually released. When it is intended to accelerate the proliferation of corneal endothelial cells or to treat a disease associated with corneal endothelial damage, it is possible to control the degradation of the gelatin hydrogel and the duration of resulting sustained release of bFGF over a range of about 1 day to 2 months; for example, the duration is preferably such that the degradation completes within about 2 weeks.

To allow gelatin hydrogel to carry bFGF, an aqueous bFGF solution may be added dropwise to the gelatin hydrogel to impregnate the gel, or the gelatin hydrogel may be suspended in an aqueous bFGF solution and re-swollen. Herein, "to carry" means that bFGF is immobilized to gelatin hydrogel by an interaction such as a Coulomb force, hydrogen bond, hydrophobic interaction, or static electricity between the gelatin hydrogel molecule and bFGF, and gets dispersed and contained in the gelatin hydrogel.

The amount of bFGF that can be contained in gelatin hydrogel varies depending on the water content of the gelatin hydrogel and the like, and can be about 0.12 to about 0.98 μg per mg (dry weight) of the gelatin hydrogel. In the present invention, the gel is preferably prepared so that the amount of bFGF will be about 0.20 to about 0.80 μg per mg of the gelatin hydrogel.

The bFGF sustained-release gelatin hydrogel particles used in the present invention, after being formulated into a preparation as required along with ordinary pharmaceutically acceptable additives (stabilizers, preservatives, solubilizers, pH regulators, thickening agents and the like), are used as a corneal endothelial cell proliferation accelerator or as a therapeutic agent for a disease associated with corneal endothelial damage. The additives used may be publicly known ones. Furthermore, a variety of additives that regulate the sustained-release effect (low-molecular substances or high-molecular substances such as amino acids, sugars having an amino group, a phosphate group, a sulfate group, an SH group, a carboxyl group or the like, lipids and the like), other active ingredients possessing the activity of enhancing the effect of bFGF or suppressing the degradation/deactivation of bFGF, and the like can also be contained. These other active ingredients are not particularly limited, as far as one of said activities is possessed; the other active ingredients may be any low-molecular substances or high-molecular substances such as polysaccharides, lipids, glycolipids, proteins, glycoproteins, peptides, a variety of low-molecular weight compounds or high-molecular weight compounds that can be utilized as drugs and the like.

The dosage form of the agent of the present invention is not particularly limited, as far as it can be administered into the anterior chamber; normally, the agent of the present invention is used in the form of bFGF sustained-release gelatin hydrogel particles as they are, or after being formulated into a preparation as a suspension of bFGF sustained-release gelatin hydrogel particles. In the latter case, bFGF sustained-release gelatin hydrogel particles are dispersed in a pharmaceutically acceptable sterile aqueous solvent (water for injection, physiological saline, a variety of buffer solutions (for example, phosphate buffer solution, carbonate buffer solution, HEPES buffer solution, Tris buffer solution and the like) and the like). The concentration of bFGF sustained-release gelatin hydrogel particles in the preparation is not particularly limited, as far as the particles can be administered into the anterior chamber, and the concentration can be adjusted as appropriate according to the disease to be treated, patient age, body weight, amount administered and the like; preferably, the concentration of bFGF in the entire preparation may range from about 0.001 to about 500 μg/mL, more preferably from about 0.1 to about 200 μg/mL.

The agent of the present invention is safe and can be administered to a mammal. Examples of the mammal include those shown above.

The agent of the present invention is characterized by being administered into the anterior chamber. When the agent is administered into the anterior chamber, bFGF is released in a sustained manner into the anterior chamber and persistently supplied to corneal endothelial cells, whereby the proliferation of corneal endothelial cells is accelerated. Administration into the anterior chamber also makes it possible to suppress the influence of bFGF on organs other than the cornea to the minimum level. Administration into the anterior chamber is performed normally by injection. Since the volume of the anterior chamber is relatively small (about 350 μL (about 300 to about 400 μL) for humans and about 250 μL (about 200 to about 300 μL) for rabbits, based on aqueous humor volume), it is preferable in administration into the anterior chamber that a given volume of aqueous humor is first drawn out from the anterior chamber using a syringe, after which the agent of the present invention in the same volume as the drawn aqueous humor is injected into the anterior chamber. As far as the amount administered is such that the ocular function is not adversely influenced, the agent of the present invention can also be injected without drawing out the aqueous humor from the anterior chamber.

The agent of the present invention is useful as a corneal endothelial cell proliferation accelerator or a therapeutic agent for a disease associated with corneal endothelial damage. Here, diseases associated with corneal endothelial damage include, for example, bullous keratopathy (for example, bullous keratopathy after intraocular surgery, after laser iridectomy, after uveitis, or after trauma), congenital hereditary corneal endothelial dystrophy, Fuchs' corneal endothelial dystrophy, corneal guttata, posterior polymorphous corneal dystrophy, iridocorneal endothelium syndrome or post-keratoplasty transplant failures and the like. The agent of the present invention is particularly useful as a therapeutic agent for bullous keratopathy.

The amount administered of the corneal endothelial cell proliferation accelerator or therapeutic agent for a disease associated with corneal endothelial damage of the present invention can be adjusted as appropriate according to the disease to be treated, patient age, body weight, and the like, and is, based on bFGF, normally about 20 to about 600 ng, preferably about 30 to about 300 ng, more preferably 45 to 100 ng (for example, about 70 ng), per eye for an adult human patient. If the amount administered is not more than about 20 ng, the effect of accelerating corneal endothelial cell proliferation could be limited; if the amount administered is not less than about 1000 ng, the risk of having side effects such as corneal opacity, neovascularization, and inflammation increases. When calculated on the basis of aqueous humor volume, the amount of bFGF administered is about 0.06 to about 1.7 ng, preferably about 0.086 to about 0.86 ng, more preferably about 0.13 to about 0.29 ng, per μL of aqueous humor, for humans. As stated above, the volume of human aqueous humor is about 300 to about 400 μL; therefore, a dose of about 70 ng per eye, based on bFGF, is equivalent to a dose of about 0.18 to about 0.23 ng per μL of aqueous humor. If the effect is insufficient with single dosing, the multiple dosing can be performed.

While the present invention is explained in more detail in the following by referring to the Examples shown below, they do not limit the present invention in any manner.

In the following Examples, PBS (phosphate buffered saline) was prepared and treated using Dulbecco PBS(−) powder manufactured by Nissui Pharmaceutical Co., Ltd., according to the instructed method of use.

EXAMPLES

Preparation Example 1

Preparation of Gelatin Hydrogel Particles

Using gelatin with isoelectric point 4.9, molecular weight 99000 kDa (manufactured by Nitta Gelatin Inc.) obtained by alkali treatment of TYPE I collagen derived from beef bones, gelatin particles were prepared by the following procedures.

An aqueous gelatin solution (10 wt %, 10 mL) heated in advance to 40° C. was dispersed in olive oil (manufactured by Wako Pure Chemical Industries, Ltd., 300 mL, heated to 40° C.) over 10 min with stirring at 400 rpm to give a water-in-oil emulsion. The obtained water-in-oil emulsion was rapidly cooled with ice and further stirred for 30 min.

The olive oil was removed by centrifugation, and gelatin particles were resuspended in acetone. They were recovered by centrifugation (5000 rpm, 4° C., 5 min), passed through a stainless mesh (aperture 75 μm), and fractionated according to the particle size by using a stainless mesh (aperture 30 μm). Then, gelatin particles were obtained by air drying at 4° C.

Glutaraldehyde was added to 0.1 wt % polyoxyethylene sorbitan monooleate (manufactured by Tokyo Chemical Industry Co., Ltd.: trade name "Tween80")/DDW to a final concentration of 0.125 wt %, and cooled to 4° C. to give a crosslinking solution.

The gelatin particles (25 mg) after air drying were dispersed in the crosslinking solution (25 mL), 25 wt % aqueous glutaraldehyde solution (62.5125 μL) was added and the mixture was stirred at 4° C. for 24 hr to chemically crosslink gelatin particles. The crosslinking solution was removed by centrifugation (5000 rpm, 4° C., 5 min) to recover gelatin hydrogel particles, which were resuspended in 100 mM glycine/ultrapure water to 1 mg/mL, and the suspension was vigorously stirred at 37° C. for 1 hr to block the aldehyde residue of glutaraldehyde.

The gelatin hydrogel particles obtained as mentioned above were washed 3 times with distilled water (50 mL), recovered by centrifugation and freeze-dried.

The shape of the gelatin hydrogel particles (hereinafter to be also referred to as MS) after freeze-drying was spherical as measured by observation with an optical microscope, and the average particle diameter was 15 μm. In addition, the in vivo degradation and absorption of the gelatin hydrogel particles in the subcutaneous tissue of the back of a mouse was examined, and it was found that the gelatin hydrogel particles were degraded and absorbed in 2 weeks.

Example 1

Administration to Normal Rabbit

Preparation of Suspension of bFGF-Containing Gelatin Hydrogel Particles in PBS (Sample)

PBS (1 mL) was added to bFGF (2 mg) to prepare a 0.2 wt % bFGF/PBS solution. To MS (2 mg) prepared in Preparation Example 1 was added the above-mentioned bFGF/PBS solution (10 μL), and the MS was allowed to swell at room temperature for 2 hr to give bFGF-containing gelatin hydrogel particles. Then, the bFGF-containing gelatin hydrogel particles were suspended in PBS (1990 μL) to give a sample. Hereinafter, the thus-obtained suspension of bFGF-containing gelatin hydrogel particle is to be referred to as FGF-MS-a (FGF-MS).

Preparation of Control Suspension of Gelatin Hydrogel Particles in PBS

MS (2 mg) prepared in Preparation Example 1 was suspended in PBS (2000 μL) to give a sample. Hereinafter to be referred to as C-MS (control MS).

(Administration Method)

Under systemic anesthesia and using a surgical microscope, each sample (100 μL) of C-MS and FGF-MS-a was administered into the anterior chamber of normal Japan white rabbits (2-2.5 kg, 5 rabbits) with a 30 G needle. At days 2, 4, 6, 8 and 10 after the administration, the anterior ocular segment was observed using a slit lamp microscope and the intraocular pressure was measured by an applanation tonometer (Pneumatonometer model 30 Classic, manufactured by Reichert). The amounts of bFGF and MS administered in the C-MS administration group and FGF-MS-a administration group per one eye are shown in Table 1.

TABLE 1

|  | bFGF [ng/eye] | MS [mg/eye] |
|---|---|---|
| C-MS | — | 0.1 |
| FGF-MS-a | 1000 | 0.1 |

(Results)

FIG. 1 shows a photograph of the anterior ocular segment of normal rabbits on day 6 from the administration of each sample. In the FGF-MS-a administration group, severe ocular surface inflammation was observed from the next day of the administration, and cornea opacity and neovascularization were observed 3 days later. This indicates a sustained release of a high concentration of bFGF in this administration group. No appreciable finding was obtained in the C-MS administration group.

Figure 2:
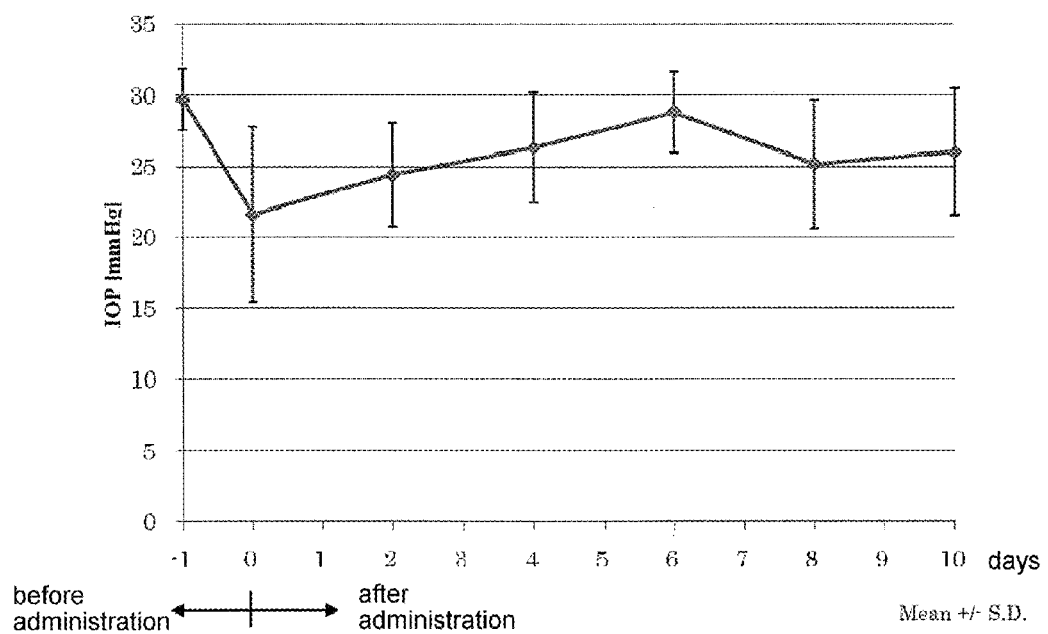
FIG. 2 shows the time-course changes of the intraocular pressure of normal rabbits after administration of C-MS.

FIG. 2 shows the time-course changes of the intraocular pressure of normal rabbits after administration of C-MS. With no increase in the intraocular pressure after administration, gelatin hydrogel particles administered into the anterior chamber were considered to be a safe drug carrier causing no clogging in the trabecular meshwork.

Preparation Example 2

An operation in the same manner as in Example 1 (Preparation of suspension of bFGF-containing gelatin hydrogel particles in PBS (sample)) except that the amounts of bFGF and PBS to be used were changed to those shown in the following Table 2 was performed to prepare FGF-MS-b, FGF-MS-c, FGF-MS-d, FGF-MS-e, FGF-MS-f and FGF-MS-g.

TABLE 2

|  | bFGF/PBS solution | | | bFGF dose [ng/eye] | MS [mg/eye] |
|---|---|---|---|---|---|
|  | bFGF (mg) | PBS (mL) | concentration (wt %) | | |
| FGF-MS-a | 2.0 | 1 | 0.2 | 1000 | 0.1 |
| FGF-MS-b | 2.0 | 10 | 0.02 | 100 | 0.1 |
| FGF-MS-c | 2.0 | 100 | 0.002 | 10 | 0.1 |
| FGF-MS-d | 2.0 | 50 | 0.004 | 20 | 0.1 |
| FGF-MS-e | 1.5 | 25 | 0.006 | 30 | 0.1 |
| FGF-MS-f | 1.8 | 20 | 0.009 | 45 | 0.1 |
| FGF-MS-g | 1.4 | 10 | 0.014 | 70 | 0.1 |

Example 2

Consideration of Optimal Dose (Method)

As samples, FGF-MS-b, FGF-MS-c and FGF-MS-e prepared in Preparation Example 2, and C-MS prepared in Example 1 were used.

Under systemic anesthesia, heparin was administered to normal Japan white rabbits (2-2.5 kg, 6 rabbits) to 1000 IU/kg body weight from the ear vein. After 20 min from the administration, a stainless probe (diameter 7 mm) cooled with liquid nitrogen was brought into contact with the corneal surface for 15 seconds to prepare a corneal endothelium disorder model by trans-corneal cryopexy. Then, each sample was administered into the anterior chamber in the same manner as in Example 1. The amounts of bFGF contained in a dose of each sample per one eye are as shown in the above-mentioned Table 2. The dose of MS was 0.1 mg/eye for both the bFGF administration group and C-MS administration group.

On day 2 from the administration, the anterior ocular segment was observed by a slit lamp microscope. Thereafter, the rabbits were euthanized and the eyeballs were isolated. The cornea was collected and stained with alizarin.

(Results)

Figure 3:
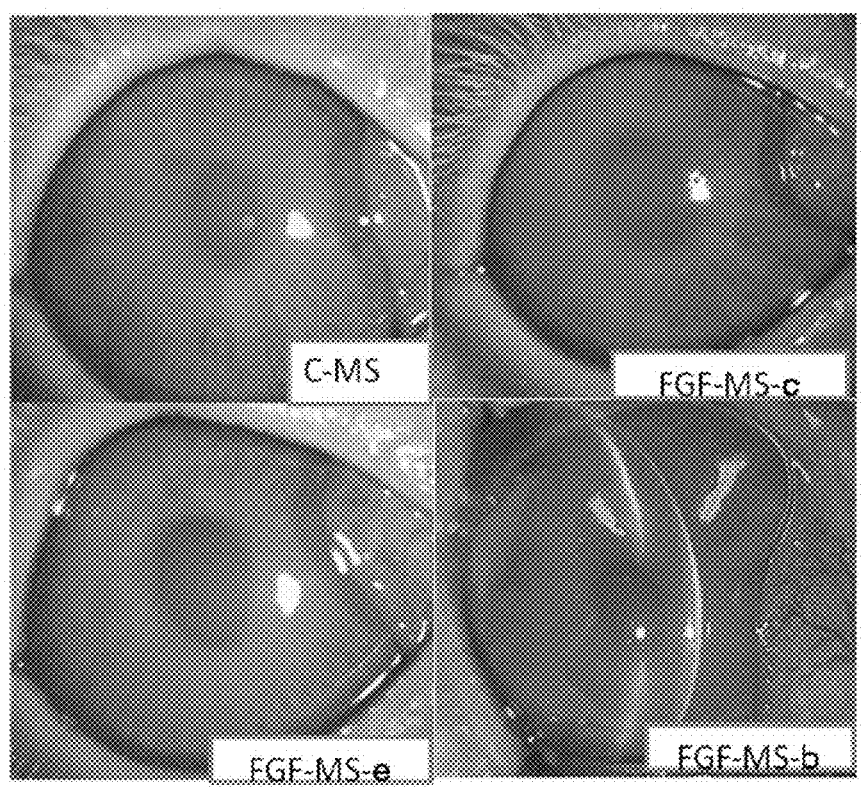
FIG. 3 is a photograph taken the next day of the administration of C-MS, FGF-MS-b, FGF-MS-c or FGF-MS-e to corneal endothelial disorder models.
Figure 4:
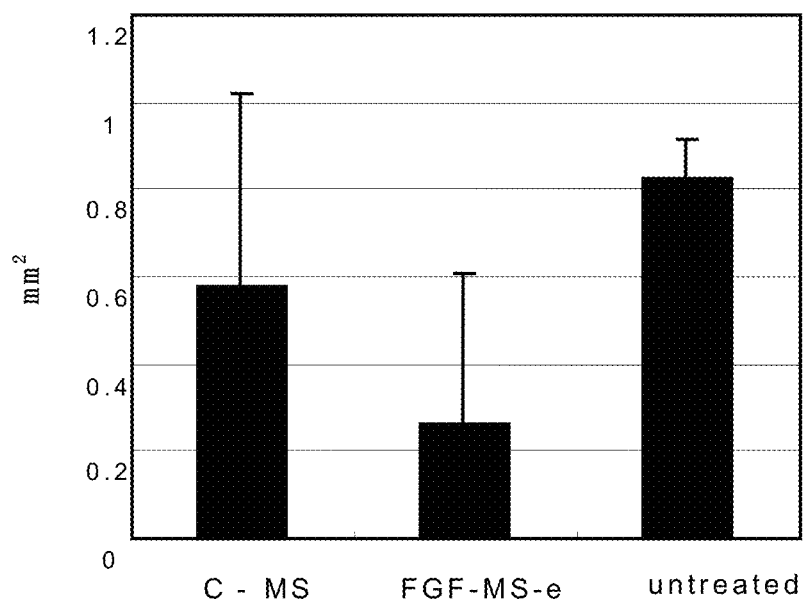
FIG. 4 shows corneal endothelium defective areas in the C-MS administration group, FGF-MS-e administration group and untreated group.

FIG. 3 shows a photograph taken the next day of the administration of C-MS, FGF-MS-b, FGF-MS-c or FGF-MS-e to corneal endothelial disorder models. In addition, Table 3 and Table 4 show corneal endothelium defective areas of each group. FIG. 4 shows corneal endothelium defective areas in the C-MS administration group, FGF-MS-e administration group and untreated group. As is clear from Tables 3, 4 and FIG. 4, administration of bFGF-containing gelatin hydrogel particles decreased the defective areas. The results have clarified the effectiveness of the bFGF-containing gelatin hydrogel particles for corneal endothelium damage.

TABLE 3

| | corneal endothelium defective area [mm$^2$] | | |
|---|---|---|---|
| | Left eye | Right eye | |
| | C-MS | FGF-MS-c | untreated |
| 1 | 1.370 | — | 0.887 |
| 2 | 0.000 | — | 0.769 |
| 3 | 0.413 | 0.775 | — |
| 4 | 0.638 | 0.000 | — |
| 5 | 0.574 | 0.093 | — |
| 6 | 0.449 | 0.177 | — |
| average | 0.57 | 0.26 | 0.83 |

TABLE 4

| | corneal endothelium defective area [mm$^2$] | | |
|---|---|---|---|
| | Left eye | Right eye | |
| | C-MS | FGF-MS-c | FGF-MS-e |
| 1 | 1.01 | — | 0.47 |
| 2 | 2.69 | — | 0.00 |
| 3 | 4.63 | 2.54 | — |
| 4 | 0.35 | 2.68 | — |
| average | 2.17 | 2.61 | 0.23 |

Example 3

Examination of Usefulness of Gelatin Hydrogel Particles (Method)

Corneal endothelium disorder models were prepared in the same manner as in Example 2, and the following samples were respectively administered into the anterior chamber in the same manner as in Example 1.

C-MS: administration of bFGF-free gelatin hydrogel particles bFGF-solution: bFGF (solution) was administered at 30 ng/eye into the anterior chamber without using a carrier. FGF-MS-e: FGF-MS-e prepared in Preparation Example 2 was administered into the anterior chamber.

The rabbits were euthanized 2 days after the administration, and the eyeballs were isolated. The cornea was collected and stained with alizarin.

(Results)

TABLE 5

| | corneal endothelium defective area [mm$^2$] | | |
|---|---|---|---|
| | Left eye | Right eye | |
| | C-MS | bFGF-solution | FGF-MS-e |
| 1 | 0.162 | 0.374 | — |
| 2 | 0.056 | 0.353 | — |
| 3 | 0.783 | — | 0.235 |
| average | 0.33 | 0.36 | 0.24 |

Figure 5:
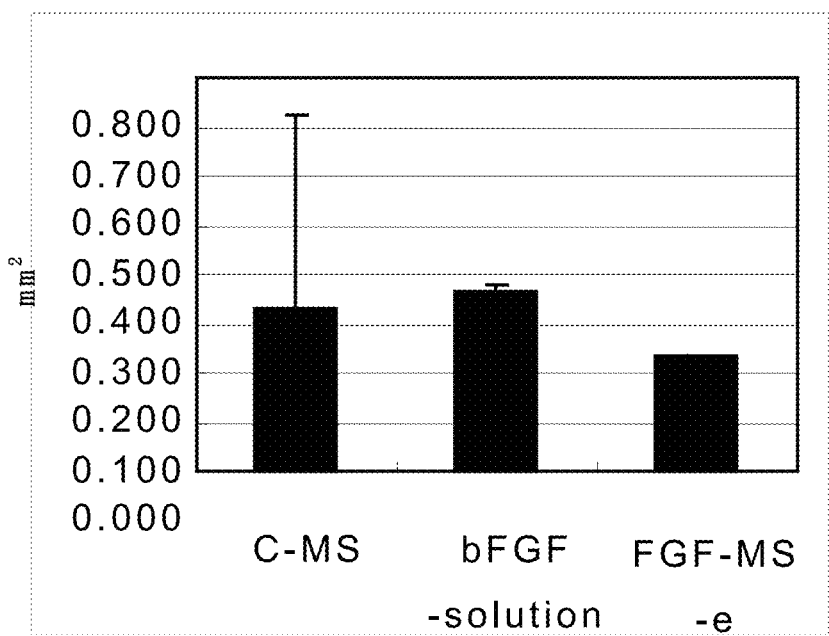
FIG. 5 shows corneal endothelium defective areas 2 days after the administration of C-MS, bFGF-solution or FGF-MS-e.

Table 5 shows corneal endothelium defective areas of C-MS, bFGF-solution and FGF-MS-e administration groups and average values thereof (unit mm$^2$). FIG. 5 shows mean±S.D. thereof. The results indicate that the treatment effect on corneal endothelium damage is enhanced by carrying bFGF on gelatin hydrogel particles.

Example 4

Examination of Optimal Dose Range (Method)

The effect of bFGF gelatin hydrogel particles on corneal endothelium damage at doses of 45 ng/eye, 70 ng/eye and 100 ng/eye was examined. Corneal endothelium disorder models were prepared in the same manner as in Example 2, and respective samples of FGF-MS-b, f, g prepared in Preparation Example 2 and C-MS prepared in Example 1 were administered into the anterior chamber in the same manner as in Example 1. The rabbits were euthanized 2 days after the administration, and the eyeballs were isolated. The cornea was collected and stained with alizarin.

(Results)

Figure 6:
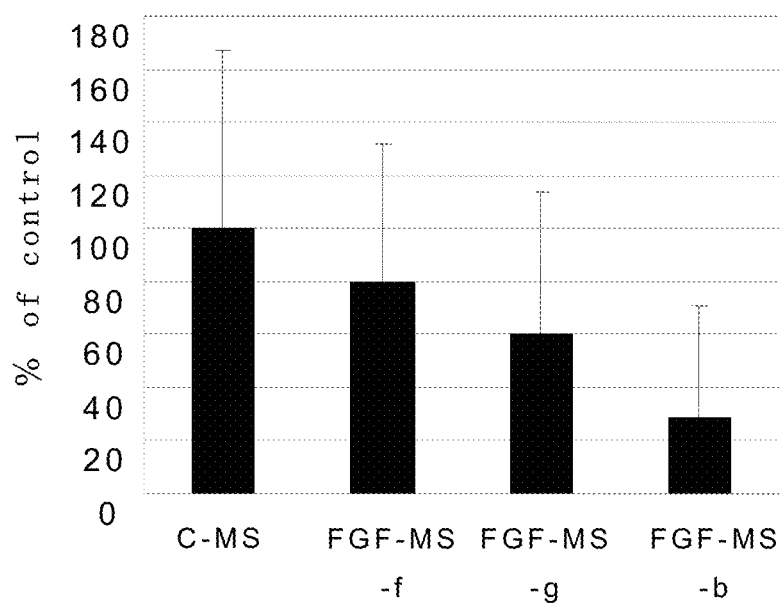
FIG. 6 shows the ratio of the corneal endothelium defective area of other sample administration group to that of the C-MS administration group as 100%.

FIG. 6 shows the ratio of the corneal endothelium defective area of other sample administration group to that of the C-MS administration group as 100%. As is clear from FIG. 6, bFGF gelatin hydrogel accelerated healing of corneal endothelium wound in a bFGF dose-dependent manner.

Example 5

Effect of Accelerating Corneal Endothelium Wound Healing (Method)

FGF-MS-e and C-MS prepared in Preparation Example 2 were used as samples. Under systemic anesthesia, heparin was administered to normal Japan white rabbits (2-2.5 kg, 4 rabbits) to 1000 IU/kg body weight from the ear vein. After 20 min from the administration, a stainless probe (diameter 7 mm) cooled with liquid nitrogen was brought into contact with the corneal surface for 15 seconds to prepare a corneal endothelium disorder model by trans-corneal cryopexy. In the same manner as in Example 1, each sample was administered into the anterior chamber.

On day 2 from the administration, the anterior ocular segment was observed by a slit lamp microscope. Thereafter, the rabbits were euthanized and the eyeballs were isolated. The cornea was fixed with PFA (para-formaldehyde) and subjected to alizarin staining and Ki67 immunostaining.

(Results)

Figure 7:
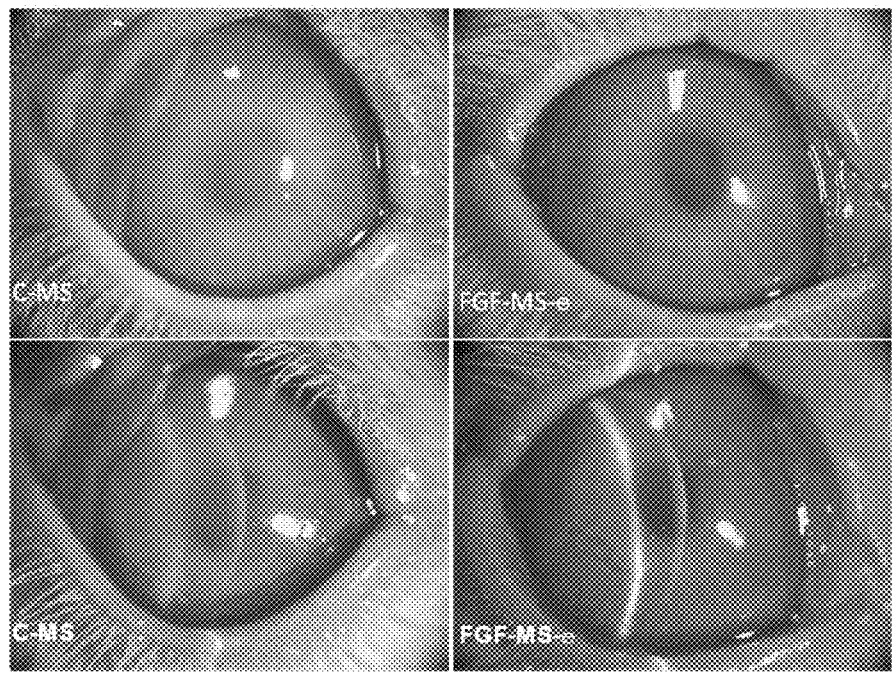
FIG. 7 is a photograph of the anterior ocular segment 2 days after the administration of C-MS or FGF-MS-e.
Figure 8:
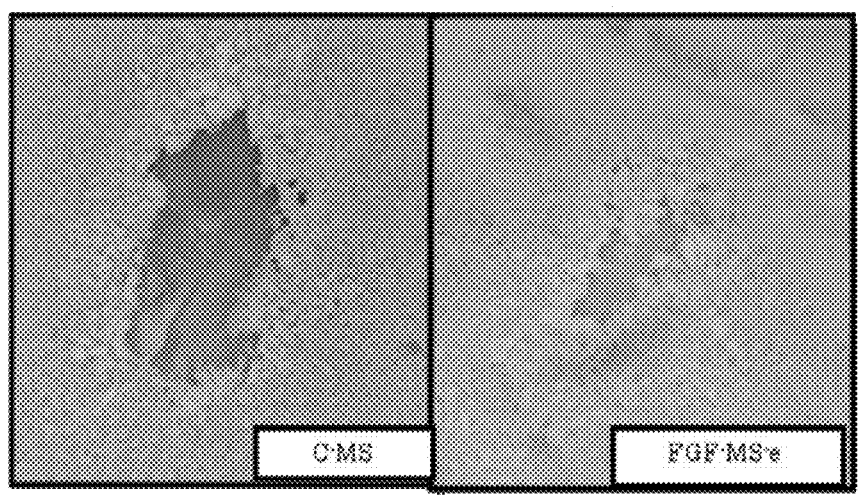
FIG. 8 shows alizarin-stained corneal endothelial surface 2 days after the administration of C-MS or FGF-MS-e.
Figure 9:
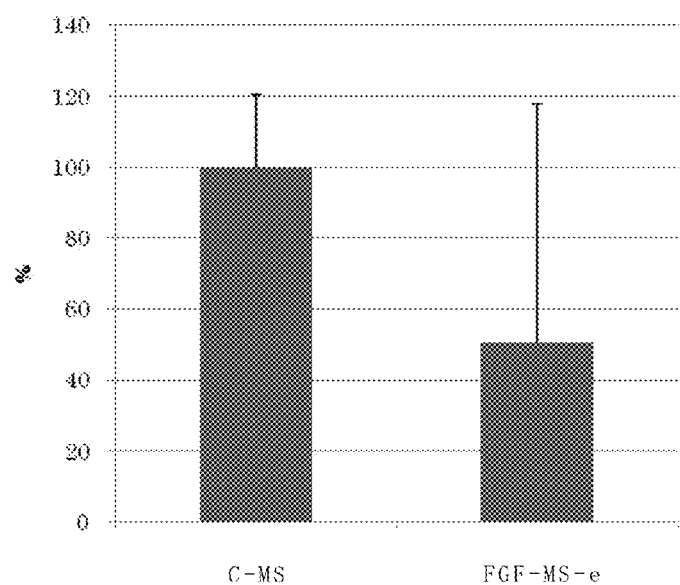
FIG. 9 shows the ratio of the corneal endothelium defective area of FGF-MS-e administration group to that of the C-MS administration group as 100%.
Figure 10:
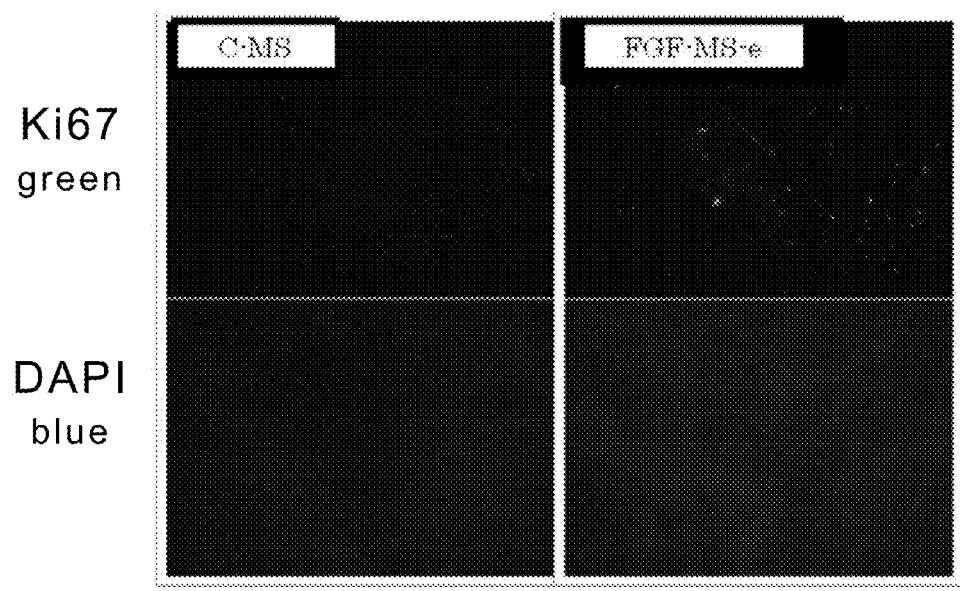
FIG. 10 shows Ki67-stained corneal endothelial surface 2 days after the administration of C-MS or FGF-MS-e.

FIG. 7 shows a photograph of the anterior ocular segment 2 days after the administration of each sample. In the C-MS administration group, corneal opacity was observed and the pupillary margin was markedly unclear. On the other hand, in the FGF-MS-e administration group, corneal opacity was not observed and the pupillary margin was clearly recognized. From the observation of an optical section exposed to slit light illuminated diagonally in front, the corneal thickness increased in the C-MS administration group, indicating the onset of corneal edema. As compared thereto, the corneal thickness was small in the FGF-MS-e administration group, and corneal edema was not observed. In addition, corneal neovascularization was not observed in each group. FIG. 8 shows alizarin-stained corneal endothelial surface on day 2 from the administration of each sample. The FGF-MS-e administration group showed decrease in the corneal endothelium damage region as compared to the C-MS administration group. FIG. 9 shows the ratio of the corneal endothelium defective area of FGF-MS-e administration group to that of the C-MS administration group as 100%. As a result of the analysis, the FGF-MS-e administration group showed a significant repair accelerating effect as compared to the C-MS administration group. FIG. 10 shows Ki67-stained corneal endothelial surface on day 2 from the administration of each sample. Ki67 positive cells were observed near the corneal endothelium defective region in the FGF-MS-e administration group, indicating proliferation of the corneal endothelium cells.

Examples 1-5 have clarified that administration of bFGF-containing gelatin hydrogel particles (0.2 mg) into the anterior chamber of patients with a corneal endothelium disorder enables early repair of the corneal endothelium defective region. The presence of Ki67 positive corneal endothelium cells near the corneal endothelium defective region could be confirmed, which indicates cell proliferation during repair of the corneal endothelium defect. Gelatin hydrogel administration did not increase the intraocular pressure.

INDUSTRIAL APPLICABILITY

According to the present invention, the proliferation of corneal endothelium cells can be accelerated in a sustained manner. According to the present invention, a bFGF preparation useful for the treatment of a disease relating to corneal endothelium damage can be provided.

The invention claimed is:

1. A method of accelerating the proliferation of corneal endothelial cells in a subject without generating corneal neovascularization in the subject, comprising administering 30 to 300 ng per eye of a bFGF sustained-release gelatin hydrogel particle containing a bFGF-carrying gelatin hydrogel into the anterior chamber of the eye of the subject, thereby accelerating the proliferation of corneal endothelial cells in the subject without generating corneal neovascularization in the subject.

2. The method according to claim 1, wherein the amount of bFGF administered is 45 to 100 ng per eye.

3. A method of treating a disease associated with corneal endothelial damage in a subject without generating corneal neovascularization in the subject, comprising administering 30 to 300 ng per eye of a bFGF sustained-release gelatin hydrogel particle containing a bFGF-carrying gelatin hydrogel into the anterior chamber of the eye of the subject, thereby treating the disease associated with corneal endothelial damage in the subject without generating corneal neovascularization in the subject.

4. The method according to claim 3, wherein the disease associated with corneal endothelial damage is bullous keratopathy.

5. The method according to claim 4, wherein the amount of bFGF administered is 45 to 100 ng per eye.

6. The method according to claim 3, wherein the amount of bFGF administered is 45 to 100 ng per eye.

* * * * *